United States Patent [19]

Kamen et al.

[11] Patent Number: 5,066,486

[45] Date of Patent: Nov. 19, 1991

[54] METHOD FOR PREPARING COSMETIC PRODUCTS AND THE PRODUCTS OBTAINED THEREBY

[75] Inventors: Melvin E. Kamen, Highlands; Philip Bernstein, Glen Ridge, both of N.J.

[73] Assignee: Revlon, Inc., New York, N.Y.

[21] Appl. No.: 497,277

[22] Filed: Mar. 22, 1990

Related U.S. Application Data

[63] Continuation-in-part of Ser. No. 258,219, Oct. 14, 1988, Pat. No. 4,938,952.

[51] Int. Cl.$^5$ .................... A61K 7/021; A61K 7/027; A61K 7/032
[52] U.S. Cl. .................................. 424/63; 424/64; 424/69; 424/83
[58] Field of Search .................... 424/64, 83, 69, 63, 424/78

[56] References Cited

U.S. PATENT DOCUMENTS

| | | | |
|---|---|---|---|
| 3,479,429 | 11/1969 | Morshauser et al. | 424/64 X |
| 3,838,092 | 9/1974 | Vogt et al. | 524/546 |
| 4,332,698 | 6/1982 | Bernstein | 502/4 |
| 4,358,396 | 11/1982 | Bernstein | 502/159 |
| 4,367,220 | 1/1983 | Boulogne et al. | 424/64 |
| 4,396,693 | 8/1983 | Bernstein | 429/217 |
| 4,433,063 | 2/1984 | Bernstein | 502/402 |
| 4,659,562 | 4/1987 | Arraudeau | 424/63 |
| 4,699,780 | 10/1987 | Jennings et al. | 424/64 X |
| 4,743,441 | 5/1988 | Takema et al. | 424/69 X |

OTHER PUBLICATIONS

Sagarin, Cosmetics Science & Technology, Chapter 13, Lipsticks, 1957, pp. 281–285.

*Primary Examiner*—Thurman K. Page
*Assistant Examiner*—Susan S. Rucker
*Attorney, Agent, or Firm*—Julie Blackburn

[57] ABSTRACT

A cosmetic product includes a fibrillatable polymer as a binding agent. The thusly prepared composition having said fibrillatable polymer incorporated therein provides a cosmetic product which can be employed for coloration of the skin and utilized as a lipstick, as well as eyeshadow and eyeliner pencils, compressed powders and other solid-type cosmetic products obtained by suitable processing techniques such as milling, extrusion, compacting and so on.

34 Claims, No Drawings

METHOD FOR PREPARING COSMETIC PRODUCTS AND THE PRODUCTS OBTAINED THEREBY

CROSS REFERENCE TO RELATED APPLICATIONS

This application is a continuation-in-part of copending application Ser. No. 07/258,219, filed Oct. 14, 1988.

FIELD OF THE INVENTION

This invention relates to cosmetics, in general, and, more particularly, to lipstick products having incorporated therein a fibrillated polymeric, binding component.

BACKGROUND OF THE INVENTION

Cosmetics have been used since early times to beautify the skin and hair. The manufacture of cosmetics is a 20th century development under the influence of Hollywood in the 1920's coupled with the development of mass production and mass marketing techniques. As a consequence, cosmetics were offered to the public at cheap prices. As one can ascertain, the cosmetic industry today is huge, and there are a tremendous number of products utilized.

While most cosmetics are relatively simple, they contain many ingredients which are employed to formulate the various cosmetic preparations. Essentially, a cosmetic chemist employs a variety of materials which are often based on emulsified mixtures of oils, water-in-oil or oil-in-water, anhydrous ointments, water pigments, talcs and so on.

Manufacturing processes of cosmetics can normally be divided into three main categories, including lipsticks and related stick-type products such as eyeliner and eyeshadow pencils, creams and lotions, and compressed powders such as, for example, cake makeup. This application primarily relates to lipstick products and, to related stick-type cosmetic products. However, it is also readily applicable to other cosmetic products as well.

Over the years, conventional lipsticks have essentially been composed of hydrocarbonous compositions having oil-wax bases combined with colorants, fragrant components, and various other additives. The presence of the oil-wax base gives the lipstick compositions such stability or stiffness that they can be molded into desired configurations, while remaining soft enough to be readily applicable to the skin.

In general, commercially available lipstick products have proven widely successful. However, a considerable portion of many of these commercialized products have presented particular problems such as structural instability, less than desired lubricity, poor moisture resistance, and relatively short storageability. Various manufacturing techniques, particularly modification of the respective lipstick formulations, have been employed to overcome the afore-mentioned shortcomings. Many of these techniques apply to cosmetic products, in general.

Among the techniques which have been proposed to improve cosmetic products are included the addition of binders such as that in Arraudeau, et al. U.S. Pat. No. 4,659,562. The foregoing reference teaches the use of a binding agent comprised of co-pulverized finely divided fibers of polyethylene and silica. The resultant copulverized mixture of defibrillated polyethylene and silica of which the particle size has been reduced is admixed with a cosmetic make-up composition.

Still other prior art such as Boulogne, et al. U.S. Pat. No. 4,367,220 teaches the use of a liposoluble polymer having vinyl ester units therein, in combination with 1-docosanoyloxy-3 (2-ethyl)-hexyloxy-2-propanol and a 2-(lanolin alcohol derivative substituted) 1-decanylpolyethanol and a non-toxic coloring material to prepare a lipstick composition.

Jennings et al., U.S. Pat. No. 4,699,780 teaches the use of a polymeric resin derived from an isomeric or silicalkylene monomer and polyalkylalkane or a polyhydroxyalkane and a polysiloxane to prepare a cosmetic composition.

Takema et al. U.S. Pat. No. 4,743,441 teaches the use of a polyvinylalcohol and an alkylvinylether copolymer in a film forming cosmetic composition.

SUMMARY OF THE INVENTION

A cosmetic product comprising a prescribed quantity of an original cosmetic product or the formulation thereof, having a fibrillated polymer binding agent incorporated therein; said quantity of the actual formulation of the original cosmetic product being sufficient to yield a readily useful improved cosmetic product. The resultant product displays desired characteristics such as improved coloration, increased lubricity, greater moisture resistance and other properties superior to those of the prior art.

The present invention, is especially suitable for the use in the production of molded lipsticks. Accordingly, the invention will be described, in connection with the preparation of molded lipstick products.

DETAILED DESCRIPTION OF THE INVENTION

It is believed that this specification does not require drawings as the products and compositions are adequately described and understood.

As is known, certain polymers have the capability of fibrillation. According to the techniques of the present invention, it is advantageous for the polymer to be fibrillatable in a dry-type process. In any event, such polymers are known. For example, polytetrafluoroethylene (PTFE) can be fibrillated from a dry powder and is commercially available as duPont's Teflon 6A and 7A. Fibrillatable polypropylene is also commercially available, for example, as strands, tapes or films which can be used as such or cut to appropriate sizes.

As will be further understood, according to the techniques of the present invention, these fibrillatable polymers are employed as a binder for a cosmetic product. The polymer, when fibrillated, explodes into strands or fibers which form matrices that encompass the particles of the various components of the cosmetic product composition. Said components are held in intimate contact with the polymer fibers and can be applied therewith to the skin to provide a unique type of cosmetic product. The strands of fiber or fibrils encradle to form a matrix which binds the particles of the various components that make-up the cosmetic product.

As indicated, polytetrafluoroethylene (PTFE) is a fluorocarbon resin which fibrillates when the PTFE powder is exposed to shear. This is done with an extreme change in temperature or change in the pH level of the admixing system. For example, duPont manufactures a PTFE as Teflon 7A which is a powder of high bulk density usually used to mold large shapes. It has been discovered that when Teflon 7A is placed in a high shear mixer, such as a Waring blender, and mixed for two minutes, the powder is converted to a fibrillated mass. When these fibers are compacted or compressed they hold the shape of any container in which they were compressed. Thus one can make a mixture of a blended cosmetic product composition and an amount of fibrillated Teflon in concentrations ranging between 1 and 25%, by weight, of the total composition.

Other processing techniques will operate as well such as milling, extruding and injection molding of the fibril bonded cosmetic product composition. Milling the cosmetic product composition and PTFE combination produces a homogeneous mixture which can be molded into desired configurations or otherwise formed into sheets of materials which are then die cut into various shapes. One can also extrude the mixture to obtain cylinders of material which are cut into various desired lengths useful in, for example, the manufacturing of cosmetic pencils, and other stick-type products. The mixture can be pelletized to provide cosmetic pellets for skin coloration or other purposes. The use of the polymeric fibers has applications in various other cosmetic product preparations such as, eye shadows, eye liners, creams and other non-stick-type cosmetics and toiletries. It is of course understood that a perfume or fragrance can be added to the cosmetic product composition to impart a desired aroma to the same. It is understood that other polymers which are capable of fibrillation, such as polypropylene and so on, can also be used.

As one can ascertain from the above, the processing techniques are as considerably simple as utilizing a mechanical blending process whereby, based on the nature of the polymer, no additional binders are necessary. The resulting product is extremely smooth to the touch and is capable of easy and smooth application. The combination of the Teflon fibers and the formulated cosmetic product can be extruded to produce, for example, sheets which can then be cut by means of die cutting techniques to provide various cosmetic shapes which will impart the desired aesthetic characteristics such as color to the skin of the consumer. Thus, the improved cosmetic products can be extruded, milled, compressed or injection molded, and yet, according to this invention maintain their structural integrity.

Due to the properties of the PTFE, the final cosmetic product is relatively hydrophobic or waterproof when compared to similar products of the prior art. One can employ any of the conventional cosmetic product formulations which are presently utilized in manufacturing techniques for the respective commercial preparations of pressed powder or planar sheet-type cosmetic products as well as those of stick-type form. The amount of PTFE employed is between 1-25% by weight of the product with the remainder being the cosmetic product composition. These percentages can be varied according to the particular product desired.

The improved cosmetic product is relatively stick free, water resistant and lubricious. The use of the fiber matrix completely eliminates the necessity for any additional binder to be utilized. Thus, as one can ascertain, the product consists completely of a cosmetic composition having the fibrillated polymer binder incorporated therein.

Additionally, because of the inert nature of the polymeric binders, they can be utilized with numerous other cosmetic product components, without adversely affecting the formulation. One can compress and mold the mixture to form different products. For example, the material can be fabricated into sticks employing a ram extrusion technique which essentially compacts the material in a cylinder, and then a die is used to force the material out of the cylinder through a suitable aperture. The combination of the cosmetic product composition and the polymer has the appearance of a cylinder of colored cosmetic material or appears as a piece of colored chalk. This improved cosmetic product, having all the attributes indicated above, can be applied directly to the skin and exhibit an extremely smooth feeling.

As previously indicated, this invention employs a fibrillatable polymeric binder, in combination with a quantity of the original formulation of the cosmetic product. The foregoing ingredients, in prescribed ratios, with respect to one another, are slowly admixed at a controlled temperature, to produce a homogeneous, moldable composition. The novel combination of the material, the cosmetic product and the waxy temperature control component can provide a wide range of molded, cosmetic products. The improved molded cosmetic products according to this invention are, in many respects, superior to conventional, non-modified products of the same type. For example, in the case of lipsticks, the products prepared according to this invention, not only display the true color but will also be easily applied to the skin, and more resistant to moisture and temperature than commercially available lipsticks.

As discussed in Cosmetics, Science and Technology by Balsam, Sagarin et al., Second Edition (1972) pp. 382–386, a typical preparation of a conventional lipstick product would initially involve the dispersion of the colorant(s), i.e. a homogeneous mixture. The colorants are usually commercially available pigments supplied as powders. The mixture is usually milled on a roller mill or a colloid mill to avoid the formation of non-dispersed agglomerates resultant of the extremely small particle size of the powderous pigment. The problem of agglomeration of the minute pigment particles is usually avoided by the use of a thin oil to facilitate dispersion followed by the addition of a thicker oil such as castor oil to prevent settling prior to grinding. Modern manufacturing techniques have advanced to the point where the pigment can be adequately dispersed within the entire base composition prior to the introduction of all the wax by use of an ointment mill or roller mill or any other suitable mill.

Subsequent to the dispersion of the colorant as briefly discussed hereinabove, the complete lipstick formulation is admixed in a jacketed kettle, under heat and slow to moderate stirring, whereupon the perfume component is added. Upon complete melting, the mixture is allowed to stand for 20 to 30 minutes under slow agitation or heated under vacuum to eliminate any entrapped air.

Modern large scale manufacturing of lipstick products is usually achieved by use of either fully automatic molding systems wherein the molded lipstick is ejected from the mold cavity by air pressure or, semi-automatic molding systems in which the molded lipsticks are removed by hand.

In accordance with this invention, the lipstick base formulations essentially comprise, based on total weight, 60–75 percent oil, 20–25 percent wax, 5–10 percent fatty material, 5–10 percent polyhydroxy alcohol, and at least from 5 to 10 percent color additive(s).

Among the useful waxes are included carnauba wax, candelilla wax, beeswax, ozokerites, amorphous hydrocarbon waxes, paraffins, synthetic waxes, hydrogenated castor oil, spermaceti, cetyl alcohol, stearyl alcohol and mixtures thereof. The hydrocarbon waxes include those compounds which are capable of altering the melt temperature of the original cosmetic formulation to a level more compatible with that at which "in situ" fibrillation occurs.

Among the useful oils are included, vegetable oils, mineral oils, castor oil, and mixtures thereof.

Among the useful fats, are included cocoa butter, hydrogenated vegetable oil, petrolatum, lanolin, and mixtures thereof.

The pigment components useful in the preparation of the lipstick products disclosed herein are those most widely utilized for coloration in cosmetic products. Such pigments can be inorganic or organic. For example. suitable pigments include carmine, bismuth oxychloride, zinc oxide, ferric oxide, ferrous oxide, kaolin, ultramarine violet-3519, ultramarine blue, chromium oxide, chromium hydroxide, zinc oxide, silica and manganese violet. Other examples include the Federal Food and Drug Administration approved lakes of organic colorants such as FD & C Red No. 7 calcium lake, FD & C Yellow No. 5 aluminum lake, D & C Red No. 9 barium lake, and D & C Red No. 30. Additional examples include talc, mica, titanium dioxide; and any of the foregoing carried on the surface of talc, mica, or titanium oxide; and titanated mica. The term "pigment" includes mixtures of two or more of the foregoing.

As indicated hereinabove, the practice of this invention calls for the use of a fibrillated polymer or a "fibrillatable polymer," i.e. a polymer which is capable of being fibrillated, in order to function as a binder for an oil-wax base cosmetic composition. More precisely, it is imperative that the polymeric binder, in its ultimately intended form as incorporated within the formulation of the cosmetic product, be fibrillated to thereby encradle the particles of the various additional components. Accordingly, the useful polymeric binding agent may be utilized in either a fibrillated state or that wherein fibrillation occurs, in situ, i.e. during admixing. Hence, in the latter situation, a considerably greater shear force generated by a mixing blade rotated at a speed of between 500 and 1000 rpm, may be required, in order to assure adequate fibrillation of the polymeric binding material.

The procedural steps for preparing the improved cosmetic products, in accordance with this invention, entail combining or admixing either the fibrillated polymer or the fibrillatable polymer binder and a quantity of the original cosmetic product or the formulation therefor; stirring and heating to form a homogeneous molten product; decanting the resultant product into a suitable mold; and cooling the thusly improved molded cosmetic product. Consistent with the foregoing procedure, a typical lipstick shaped product, would comprise, by weight, of the total composition, about 50 parts of a conventional lipstick formulation with about 25 parts each of polyethylenetetraflouride and ceresin wax. The mixture is then heated to about 95 degrees or to the resultant temperature until the mixture becomes a melt; The melt is then poured into a conventional lipstick mold; and thereafter cooled by a suitable means such as a "chilling table". Upon removal from the mold, the resultant lipstick-shaped products yield an excellent payoff, as well as, display outstanding physical characteristics, particularly, with respect to color and applicability to and removability from the skin and prolonged storageability. Accordingly, the procedural steps and amounts for the preparation of other cosmetic products such as a lipstick and an eyeliner pencil would be the same, except the formulation of the core of the eyeliner pencil would be utilized in place of that of the lipstick product.

Regarding the ratios of the basic ingredients utilized in the practice of this invention, the actual cosmetic product or the formulation thereof can range from about 75 to about 99 percent, by weight, of the total composition. More precisely, an ideal composition would comprise about 75 percent, by weight, of the actual cosmetic product, including at least one cosmetic pigment such as ultraviolet marine, titanium or iron oxides.

Obviously, the usefulness of the improved cosmetic products prepared according to this invention will depend on the overall compatibility of the components within the respective compositions of said products having the fibrillated polymeric binder material therein and the physical properties thereof. An additional consideration would be that of the practicality, i.e. need for such products and the usefulness thereof.

As an alternate embodiment in the practice of this invention, the polymeric binding material may be fibrillated during admixing with the oil-wax based cosmetic composition. The procedure of simultaneously admixing and fibrillating the polymer binder affords an "in situ", alternate method for preparing the improved cosmetic products according to this invention. Obviously, the use of a suitable, commercially available fibrillated polymer affords a preferred, short-cut method for practicing this invention as opposed to the similar use of a fibrillatable polymer.

The following Example further illustrates certain aspects of the present invention and are not intended to limit the scope thereof to such.

EXAMPLE

A series of improved, oil-wax based lipsticks products having a fibrillated polymer binding agent therein were prepared, in accordance with this invention. A conventional lipstick formulation and the technique for the preparation thereof were utilized to form the moldable pomade to which an amount of the fibrillated, polymeric binder, consistent with the present invention, was added. The lipstick-based formulation essentially comprised about 65 percent, by weight, of mineral oil, about 20 percent of candelilla wax, 5 percent of a fatty material, about 5 percent of polyhydroxyalcohol, and about 5 percent of a color additive.

The above-described components were admixed, under slow agitation and heating, in a jacketed kettle provided with both agitation and heating means, to insure thorough melting and blending. Upon completion of melting and blending, a conventional perfume was added to the melt, as agitation continued at about 85° Centigrade. Thereafter the temperature was adjusted and maintained at about 85°-90° Centigrade, as a prescribed amount of fibrillated PTFE was stirred into the melt contents of the kettle. The amount of PTFE was approximately 3%, by weight, of that composition of the total of the original melt blend.

Quantities of the above-described hot modified lipstick pomade were then utilized to prepare lipsticks as defined by this invention, using a conventional automatic lipstick molding system. Subsequent to being cooled on a "chilling table", the thusly molded lipsticks were removed, i.e. ejected from the mold cavities, by means of a blast of air into conventional lipstick bases, i.e. handles.

Upon comparison to a conventional non-modified lipsticks comprised of the original formulation, without the fibrillated PTFE binder, it was observed that the recovered lipsticks displayed a color truly identical to that of said non-modified lipsticks. It was further observed that the surfaces of the respective lipstick were uniformly smooth and identical in all other respects, to those of the conventional, non-modified lipsticks.

The above-described improved lipsticks having the fibrillated PTFE binder therein were subsequently further evaluated on the basis of their physical properties such as firmness, applicability to the skin, and ability to yield a desired payoff. Accordingly, the lipsticks tested displayed greatly improved physical strength, without any decrease in payoff, i.e. applicability.

Summarizing, it is thus seen that this invention provides alternate, novel methods for preparing molded, cosmetic products and the improved products obtained thereby. Depending on the preferred finish and the commensurate method utilized thereof, the improved molded cosmetic products herein exhibit aesthetically desired surface characteristics superior to those of the prior art. As a result of the incorporation of the fibrillated polymeric binder, in accordance with this invention, the improved cosmetic products are characterized by their resultant uniformly smooth surfaces, their firmness, i.e. stability, applicability to the skin, ability to yield the desired payoff, improved moisture resistance, and their prolonged storage life.

Based on the disclosure set forth hereinabove, it will be understood that the embodiments described herein are merely exemplary. It will become apparent to those skilled in the art that various modifications in procedures, proportions, and materials may be made, without departing from the spirit and scope of the invention as defined by the following claims.

We claim:

1. A method for preparing an improved cosmetic lipstick or pencil comprising the steps of:
   a) admixing 1-25% of a binding agent consisting of a fibrillated polymer and 75-99% of a cosmetic composition comprising at least one wax and at least one hydrocarbon oil, to form a homogeneous mixture, and
   b) forming the resultant mixture of said fibrillated polymeric binding agent and said cosmetic composition into a cosmetic lipstick or pencil.

2. The method according to claim 1 wherein said fibrillated polymeric binding agent is polytetrafluoroethylene (PTFE).

3. The method according to claim 1 wherein the step of admixing said fibrillated polymeric binding agent and said cosmetic composition is carried out by means of a mill.

4. The method according to claim 1 wherein the step of admixing includes blending said fibrillated polymer with said cosmetic composition at a temperature ranging from 85 to 90° Centigrade.

5. The method according to claim 1 wherein said cosmetic composition contains 5-10% of a cosmetic pigment component.

6. The method according to claim 5 wherein said cosmetic pigment component is selected from the group consisting of carmine, bismuth oxychloride, zinc oxide, ferric oxide, ferrous oxide, kaolin, ultramarine violet, ultramarine blue, chromium oxide, chromium hydroxide, zinc oxide, silica, manganese violet; the lakes of organic colorants; talc, mica, titanium dioxide; any of the foregoing carried on the surface of talc, mica, or titanium oxide; and titanated mica; and mixtures of two or more of the foregoing pigments.

7. The method according to claim 5 wherein said cosmetic pigment component comprises 5-10% of the total weight of the mixture.

8. The method of claim 1 wherein the cosmetic composition comprises about 60-75% hydrocarbon oil and 20-25% wax.

9. The method of claim 8 wherein the cosmetic composition further comprises 5-10% polyhydroxy alcohol.

10. An improved cosmetic product which is a lipstick or pencil prepared by:
    a) admixing 1-25% of a binding agent consisting of a fibrillated polymer and about 75-99% of a cosmetic composition comprising at least one wax and one hydrocarbon oil;
    b) forming the resultant admixture of said fibrillated polymeric binding agent and said cosmetic composition into a cosmetic lipstick or pencil.

11. The improved cosmetic product according to claim 10 wherein said fibrillated polymeric binding agent is polytetrafluoroethylene (PTFE).

12. The improved cosmetic product according to claim 10 wherein said cosmetic composition is a lipstick composition comprising 60-75% oil and 29-25% wax.

13. The cosmetic product of claim 12 comprising 5-10% polyhydroxyalcohol.

14. The improved cosmetic product according to claim 12 wherein said cosmetic composition further includes 5-10% of a polyhydroxy alcohol, and a cosmetic pigment component.

15. The improved cosmetic product according to claim 14 wherein said cosmetic pigment is iron oxide.

16. The improved cosmetic product according to claim 14 wherein said cosmetic pigment is ultramarine violet.

17. The improved cosmetic product according to claim 14 wherein said pigment component is selected from the group consisting of carmine, bismuth oxychloride, zinc oxide, ferric oxide, ferrous oxide, kaolin, ultramarine violet, ultramarine blue, chromium oxide, chromium hydroxide, zinc oxide, silica, manganese violet; the lakes of organic colorants; talc, mica, titanium dioxide; any of the foregoing carried on the surface of talc, mica, or titanium oxide; and titanated mica; and mixtures of two or more of the foregoing.

18. An improved cosmetic lipstick or pencil product comprising 1-25% of a binding agent consisting of a fibrillated polymer and about 75-99% of a cosmetic composition comprising at least one wax and at least one hydrocarbon oil.

19. The improved cosmetic product according to claim 18 wherein said cosmetic product comprises between 1-25% by weight of said fibrillated polymer with the remainder being said cosmetic composition.

20. The improved cosmetic product according to claim 18 wherein said cosmetic composition further includes 5-10% of a polyhydroxyalcohol and 5-10% of a pigment component.

21. The improved cosmetic product of claim 18 wherein said cosmetic composition is a lipstick.

22. The improved cosmetic product according to claim 18 wherein said polymer is PTFE.

23. An improved cosmetic product which is a lipstick or pencil comprising 1-25% of a binding agent consisting of a fibrillated PTFE and 75-99% of a cosmetic composition comprising at least one wax and at least one hydrocarbon oil.

24. A method for preparing an improved cosmetic lipstick or pencil comprising the steps of:
   a) admixing 1-25% of a binding agent consisting of a fibrillatable polymer and 75-99% of a cosmetic composition comprising at least one wax and at least one hydrocarbon oil at a temperature of 85-90° C.,
   b) subjecting the mixture obtained in step
   c) To a shear force generated by a mixing blade rotated at a speed of between 500 and 1000 rpm so as to fibrillate said binding agent and thereby cause the resultant fibrillated polymeric binding agent and said cosmetic composition to form a homogenous mixture,
   d) forming the resultant mixture of said fibrillated polymer and said cosmetic composition into a cosmetic lipstick or pencil.

25. The method according to claim 24 wherein said fibrillatable polymeric binding agent is polytetrafluoroethylene (PTFE).

26. The method according to claim 24 employing between 1-25%, by weight, of said fibrillated polymeric binding agent and 65% of said cosmetic composition, including 10% of a cosmetic pigment.

27. The method according to claim 24 wherein the step of admixing said fibrillated polymeric binding agent and oil-wax base composition is carried out by means of a mill.

28. The method according to claim 24 wherein said polymer is in a powderous form prior to fibrillation.

29. The method according to claim 24 wherein said cosmetic composition contains 5-10% of a cosmetic pigment component.

30. The method according to claim 29 wherein said pigment component is selected from the group consisting of carmine, bismuth oxychloride, zinc oxide, ferric oxide, ferrous oxide, kaolin, ultamarine violet, ultramarine blue, chromium oxide, chromium hydroxide, zinc oxide, silica, manganese violet; the lakes of organic colorants; surface of talc, mica, or titanium oxide; and titanated mica; and mixtures of two or more of the foregoing.

31. An improved cosmetic lipstick or pencil prepared by:
   a) admixing 1-25% of a binding agent consisting of a fibrillatable polymer and 75-99% of a cosmetic composition comprising at least one wax and at least one hydrocarbon oil,
   b) subjecting the mixture obtained in step a) to a shear force generated by a mixing blade rotated at a speed of between about 500 and 1000 rpm so as to fibrillate said binding agent and thereby cause the resultant fibrillated polymeric binding agent to form a homogeneous mixture, and
   c) forming the resultant admixture of said fibrillated polymeric binding agent and an oil-wax based composition into a cosmetic lipstick or pencil.

32. The improved cosmetic lipstick or pencil according to claim 31 wherein said fibrillatable polymeric binding agent consists of polytetrafluoroethylene (PTFE).

33. The improved cosmetic product according to claim 31 wherein said product comprises between 1-25% by weight of said fibrillatable polymeric binding agent with the remainder being said hydrocarbonous based composition.

34. The improved cosmetic lipstick or pencil according to claim 31 wherein said cosmetic composition further includes 5-10% of a polyhydroxyalcohol, and 5-10% of a pigment component.

* * * * *